United States Patent [19]

Ozeki et al.

[11] Patent Number: 5,442,051
[45] Date of Patent: Aug. 15, 1995

[54] ANHYDROUS CRYSTAL OF 4-CARBAMOYL-1-β-D-RIBOFURANOSYL IMIDAZOLIUM-5-OLEATE

[75] Inventors: Shinji Ozeki, Ohito; Shinichi Nakatsugawa, Shizuoka, both of Japan

[73] Assignee: Asahi Kasei Kogyo Kabushiki Kaisha, Osaka, Japan

[21] Appl. No.: 231,011

[22] Filed: Apr. 21, 1994

Related U.S. Application Data

[63] Continuation of Ser. No. 61,764, Feb. 11, 1993, abandoned, which is a continuation of Ser. No. 600,617, Oct. 22, 1990, abandoned.

[30] Foreign Application Priority Data

Nov. 10, 1989 [JP] Japan .................. 1-291078

[51] Int. Cl.⁶ ............................ C07H 19/052
[52] U.S. Cl. ..................... 536/28.9; 536/28.6; 536/28.7; 536/28.8; 435/85; 435/911
[58] Field of Search ............... 536/28.6, 28.7, 28.8, 536/28.9; 435/85, 911

[56] References Cited

U.S. PATENT DOCUMENTS 3,888,843 6/1975 Mizuno et al. .................. 536/28.9

FOREIGN PATENT DOCUMENTS 121275 9/1975 Japan .
1693 1/1976 Japan .

OTHER PUBLICATIONS

Chemical Abstracts, vol. 98, No. 25, 20th Jun. 1983, p. 437, abstract No. 214316w, Columbus, Ohio, US; & JP-A-58 13 395 (Ajinomoto Co., Inc.) 25 Jan. 1983 *Abstract*.
Journal of Antibiotics, vol. 27, No. 10, 1974, pp. 775–782; K. Mizuno et al: "Studies on bredinin. I. Isolation, characterization and biological properties" *The Whole Document*.
Chemical and Pharmaceutical Bulletin, vol. 23, No. 1, 1975, pp. 245–246; "Studies on bredinin. III. Chemical synthesis of bredinin (a novel imidazole nucleoside)" *The Whole Document*.
Chemical Abstracts, vol. 85, No. 1, 5th Jul. 1976, p. 317, abstract No. 3875e, Columbus, Ohio, US; & JP-A-76 01 693 (Toyo Jozo Co., Ltd.) 8 Jan. 1976 *Abstract*.

Primary Examiner—Douglas W. Robinson
Assistant Examiner—James O. Wilson
Attorney, Agent, or Firm—Young & Thompson

[57] ABSTRACT

Anhydrous crystals of 4-carbamoyl-1-β-D-ribofuranosyl imidazolium-5-olate are disclosed. The crystals possess (1) water content of 0.5% by weight or less (the Karl Fisher method), and (2) specific IR spectrum absorption peaks in the neighborhoods of 3580, 1852, 1630, 1575, and 1554 cm$^{-1}$. They are stable against heat and high humidity conditions and can easily be manufactured by using ethanol. The compound has superior immuno-suppressing activity and is thus made into preparations for oral administration.

1 Claim, 4 Drawing Sheets

ANHYDROUS CRYSTAL OF 4-CARBAMOYL-1-β-D-RIBOFURANOSYL IMIDAZOLIUM-5-OLEATE

This application is a continuation of application Ser. No. 08/061,764, filed Feb. 11, 1993, now abandoned, which is a continuation of application Ser. No. 07/600,617, filed Oct. 22, 1990 now abandoned.

BACKGROUND OF THE INVENTION

1. Field of the Invention

The present invention relates to novel anhydrous crystals of 4-carbamoyl-1-β-D-ribofuranosyl imidazolium-5-olate which can easily be prepared and have an excellent stability against heat and water.

2. Description of the Background Art

4-Carbamoyl-1-β-D-ribofuranosyl imidazolium-5-olate (hereinafter referred to as mizolibine) is a nucleic acid-related compound which has been discovered in a culture broth of *Eupenicillium brefeldianum* M-2116 (FERM P-1104). It is a weakly acidic substance which is readily soluble in water and decomposes producing brown foam at about 200° C. Various processes are known for producing mizolibine, e.g. *J. Antibiotics*, 27, (10) 775 (1974), *Chem. Pharm. Bull.*, 23, 245 (1975), Japanese Patent Laid-open Nos. 56894/1973, 1693/1976, 121275/1975, 121276/1975, and the like. All known processes produce mizolibine mono-hydrate.

Mizolibine possesses superior immuno-suppressing activity. The compound is thus widely used in clinics for suppressing denial reactions in kidney transplant and the like, and is sold under the trade mark of Bredinin (product of Toyo Jozo Co., Ltd.). Usually, the medicine is admininistered in an amount of 2-3 mg/kg/day as an initial dose and 1-2 mg/kg/day as a maintenance dose.

There are known two types of mizolibine crystals, monohydrate crystals and anhydrous crystals. Monohydrate crystals contain about 6-7% by weight of water (theoretical amount 6.5%). The IR absorption spectrum of mono-hydrate crystals measured by a double beam IR spectrophotometer (KBr method) indicates absorption peaks in the neighborhoods of 3420, 3130, 2925, 2770, 1625, 1540, 1445, 1300, 1260, 1195, 1100, 1080, 1055, 1030, 980, 873, 829, 770, 740, 725, 560 cm$^{-1}$ [*J. Antibiotics*, 27, (10), 775 (1974), Japanese Patent Laid-open No. 56894/1973].

The IR absorption spectrum of mono-hydrate crystals measured by an IR spectrophotometer of the Fourier transform type (interference method) has absorption peaks in the neighborhoods of 3422, 3323, 3122, 2947, 2913, 1689, 1617, 1548, 1444, 1385, 1297, 1208, 1154, 1140, 1107, 1080, 1062, 1035, 982, 946, 874, 843, 824, 779, 746, 724, 679, 627, 567, 482 cm$^{-1}$ (Standard deviation: ±2 cm$^{-1}$; FIG. 3). Anhydrous crystals which have conventionally been available (hereinafter referred to as "Anhydrous Crystals A") contain about 0.5% by weight of water. Their IR absorption spectrum measured by an interference-type IR spectrophotometer has absorption peaks in the neighborhoods of 3469, 3348, 3292, 3139, 3018, 2943, 2874, 1654, 1621, 1593, 1542, 1438, 1371, 1347, 1328, 1311, 1282, 1249, 1213, 1188, 1130, 1103, 1058, 1027, 978, 947, 865, 827, 777, 768, 749, 668, 645, 630, 603, 571, and 501 cm$^{-1}$ (FIG. 2).

Crystals of mizolibine monohydrate separated by conventional culture methods and chemical synthesis are, however, unstable at a higher temperature or under highly humid conditions. For instance, if mizolibine monohydrate crystals are left to stand at 65° C. in a sealed vial, they become colored to dark green and solidifies in 24 hours. Also, when mizolibine monohydrate crystals which have been dried to dehydration in vacuum at 40° C. for 48 hours in the presence of phosphorous pentoxide are placed in an open vial at 20° C. at 95% RH, the water content are restored to 6.5% which is near the theoretical water content value of the mizolibine crystals at 24 hours. A continued storage for a further 7 days makes the crystals colored to light yellowish green. Because of such unstable nature, mizolibine monohydrate crystals are unsuitable for making a medicinal preparation therefrom, and thus no such preparation is not sold in the market.

On the other hand, Anhydrous Crystals A is more stable than mono-hydrate crystals, and is thus formulated into the commercially available Bredinin tablets. Anhydrous Crystals A, however, are obtained by a complicated process, in which the crystals are deposited from a methanol medium using a small amount of Anhydrous Crystals A as seed crystals. When manufactured, the solid crystals tend to attach to the surfaces of manufacturing units and equipment. Removing the solidified crystals by washing involves a difficult task. In addition, methanol used as a medium must be sufficiently removed.

There have been no reports published concerning the polymorphism of anhydrous crystals of mizolibine.

As a result of extensive studies aiming to solve the above-mentioned problems about Anhydrous Crystals A, the present inventors have quite unexpectedly found that there was a crystal form of mizolibine other than those of monohydrate crystals and Anhydrous Crystals A. The inventors found further that this novel crystal form was extremely stable against heat and moisture, and could be produced using ethanol as a medium. In addition, the newly found crystals had an advantage in that no crystals solidify and attach to the surfaces of manufacturing apparatus and equipment, thus ensuring an easy operation for washing them. Such findings have led to the completion of the present invention.

SUMMARY OF THE INVENTION

Accordingly, an object of this invention is to provide anhydrous crystals of 4-carbamoyl-1-β-D-ribofuranosyl imidazolium-5-olate (such crystals are hereinafter referred to as "invention crystals") possessing the following characteristics:

(1) Water content determined by the Karl Fisher method 0.5% by weight or less, and
(2) Specific IR spectrum absorption peaks (measured by an interference-type IR spectrophotometer): in the neighborhoods of 3580, 1852, 1630, 1575, 1554 cm$^{-1}$ (standard deviation ±2 cm$^{-1}$).

Other objects, features and advantages of the invention will hereinafter become more readily apparent from the following description.

DETAILED DESCRIPTION OF THE INVENTION AND PREFERRED EMBODIMENTS

Figure 3:
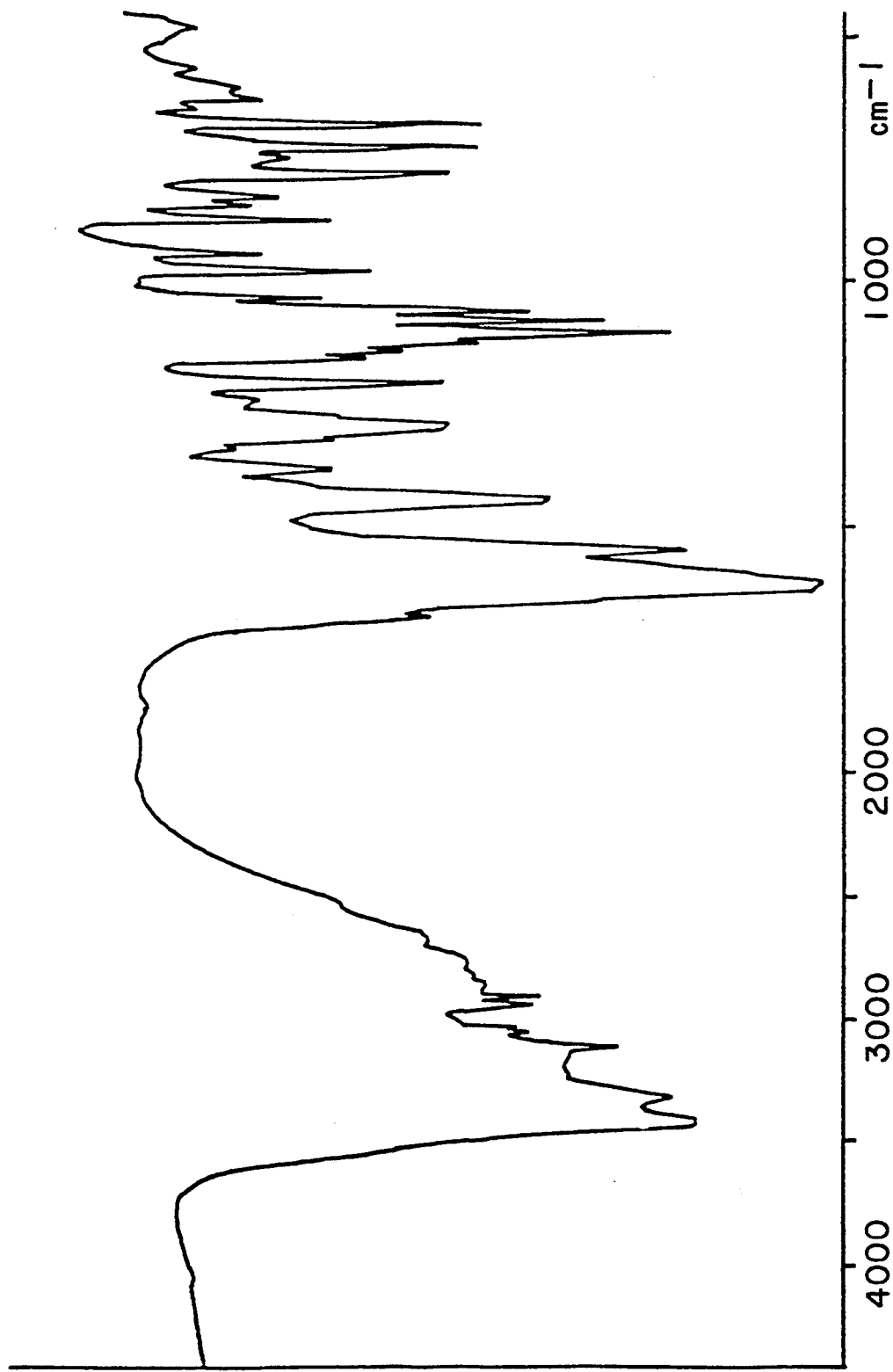
FIG. 3 is an IR absorption spectrum of monohydrous mizolibine crystals measured by an interference-type IR spectrophotometer.

Mono-hydrous crystals of mizolibine used as a raw material of the invention crystals can be produced by the above-mentioned culture method or the synthetic method. These mono-hydrous crystals contain about 6–7% of water (theoretical water content: 6.5%). The IR absorption spectrum of the crystals are as shown in FIG. 3. It is desirable that the crystals are suitably pulverized before they are added to a medium.

Ethanol used as a medium for preparing the invention crystals is that having a water content of 50% or smaller, preferably 25% or smaller, and most preferably 20% or smaller. The amount of the medium, the ethanol, used in the process of the present invention can be determined taking into account the water content of ethanol, the heating conditions, etc. Usually, 100% ethanol or ethanol of 25–0.05% water content can be used in an amount of 5 parts or more by weight, or preferably 10 parts or more by weight, per 1 part by weight of mizolibine monohydrate. No restriction is imposed as to the upper side limit of ethanol used. Taking the efficiency of the commercial manufacturing units, the upper limit may be about 50 parts by weight, and preferably 30 parts by weight.

For producing anhydrous crystals by the addition of mizolibine monohydrate to ethanol solvent, the mixture may be heated at a temperature in a range from room temperature to the temperature at which mizolibine does not decompose. Preferably, the mixture is heated at a temperature from 50° C. to the refluxing temperature of ethanol, for example, for 30 minutes to 5 hours while stirring.

The resultant solution is then cooled to a temperature at which crystals deposit, for example to below 10° C., preferably, to a temperature at which the solvent does not freeze, and especially preferably to 5°–0° C. The crystals thus produced are dried to obtain the invention crystals. There are no special restrictions as to the method by which the invention crystals are dried. They can usually be dried under reduced pressure or under vacuum at about 40° C. for 29 hours.

The invention crystals thus produced have the following characteristics.

(1) Water content 0.5% by weight or less, preferably 0.3% or less (by the Karl Fischer method).

Figure 1:
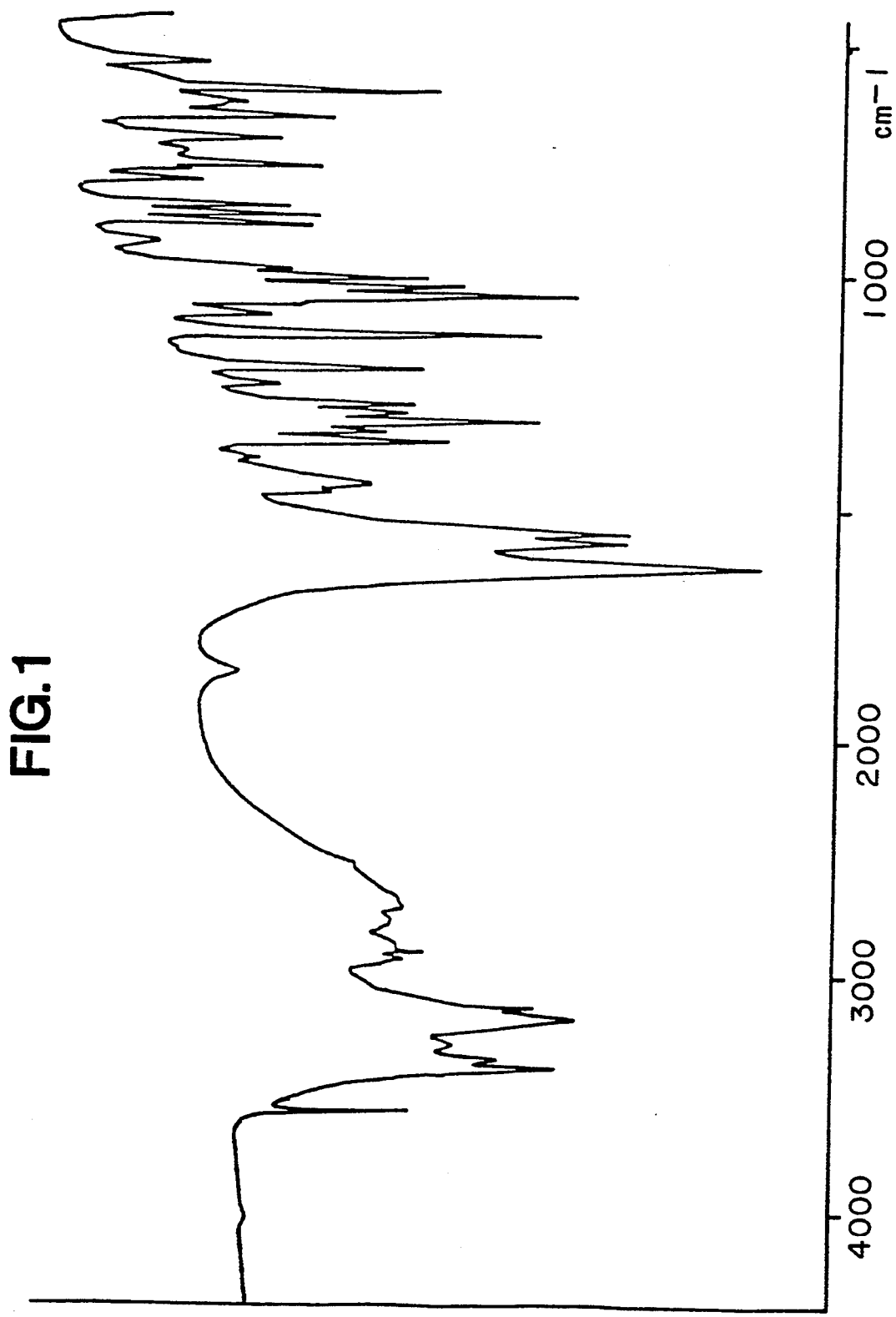
FIG. 1 is an IR absorption spectrum of anhydrous crystals of mizolibine of the present invention measured by an interference-type IR spectrophotometer.

(2) IR spectrum exhibits absorption peaks in the neighborhoods of 3580, 3397, 3355, 3192, 3142, 2901, 2712, 1852, 1630, 1575, 1554, 1448, 1360, 1339, 1320, 1229, 1280, 1238, 1204, 1133, 1093, 1047, 1031, 1011, 993, 941, 895, 878, 858, 806, 769, 713, 667, 638, 610, 555 cm$^{-1}$ (FIG. 1, measured by an interference-type IR spectrophotometer).

Of the above absorption peaks, those specific peaks existing neither in the IR absorption spectrum of Anhydrous Crystals A (FIG. 2) nor that of mono-hydrous mizolibine crystals (FIG. 3) are as follows.

3580, 1852, 1630, 1575, 1554 cm$^{-1}$.

(3) Stability (a) Heat stability

No coloration nor changes in outward appearance is observed when allowed to stand for 2 weeks at 65° C. in a sealed vial.

(b) Stability under high humidity conditions Crystals do not absorb water and are kept stable when left for 2 weeks at 95% RH and 20° C. in an open vial.

(4) Crystal form

Acicular when observed by refractory microscope.

(5) Washing conditions

The invention crystals, when attached to manufacturing apparatus and equipment, can be removed more easily than Anhydrous Crystals A.

As illustrated above, the invention crystals are extremely stable against heat and moisture, and can easily be manufactured by using ethanol which is a safe material as a medium. In addition, even if they attach as solidified crystals to the manufacturing apparatus and equipment, invention crystals can be removed very easily by washing. Thus, they can be produced without any special technique and can be prepared into a preparation for oral administration.

The crystals of the present invention can be prepared into tablets, capsules, or the like for oral administration according to a conventional method together with fillers such as anhydrous lactate, crystalline cellulose, dextran, starch, and the like, binders such as sodium carboxymethyl cellulose, methyl cellulose, ethyl cellulose, and the like, disintegrators such as potassium carboxymethyl cellulose, calcium carbonate, methyl cellulose, and the like, and lubricants such as stearic acid, magnesium stearate, talc, and the like.

Other features of the invention will become apparent in the course of the following description of the exemplary embodiments which are given for illustration of the invention and are not intended to be limiting thereof.

EXAMPLES

Comparative Example 1

Figure 4:
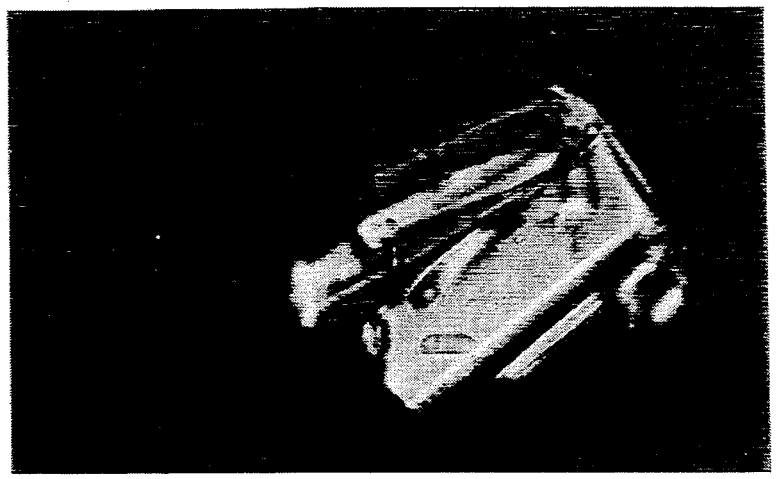
FIG. 4 is a photograph of mono-hydrous mizolibine crystals showing the crystal structure taken by a refractory microscope at 200 magnification.

To 20 g of mizolibine monohydrate was added 15 ml of water and the mixture was heated to dissolve the former. The solution was cooled and then allowed to stand overnight at 5° C. to collect deposited crystals by filtration. The crystals were left overnight at 40° C. in vacuo to dry and to obtain 18.7 g of mizolibine monohydrate crystals. To 15 g of the crystals was added 15 ml of water, followed by dissolution of the fomer by heating. 90 ml of acetone was added to the solution. The mixture was cooled at 5° C. and left overnight to collect deposited crystals by filtration. After washing with 10 ml of cold acetone, the crystals were left overnight at 40° C. in vacuo to dry and to obtain 13.4 g of purified mizolibine monohydrate crystals. IR absorption spectrum of the crystals measured by an interference-type IR spectrophotometer (the KBr method) is as shown in FIG. 3. The crystal structure of the crystals are as shown in a photograph taken by a refractory microscope at 200 magnification given in FIG. 4, wherein 1 cm correspond to 10 μm.

Comparative Example 2

Figure 2:
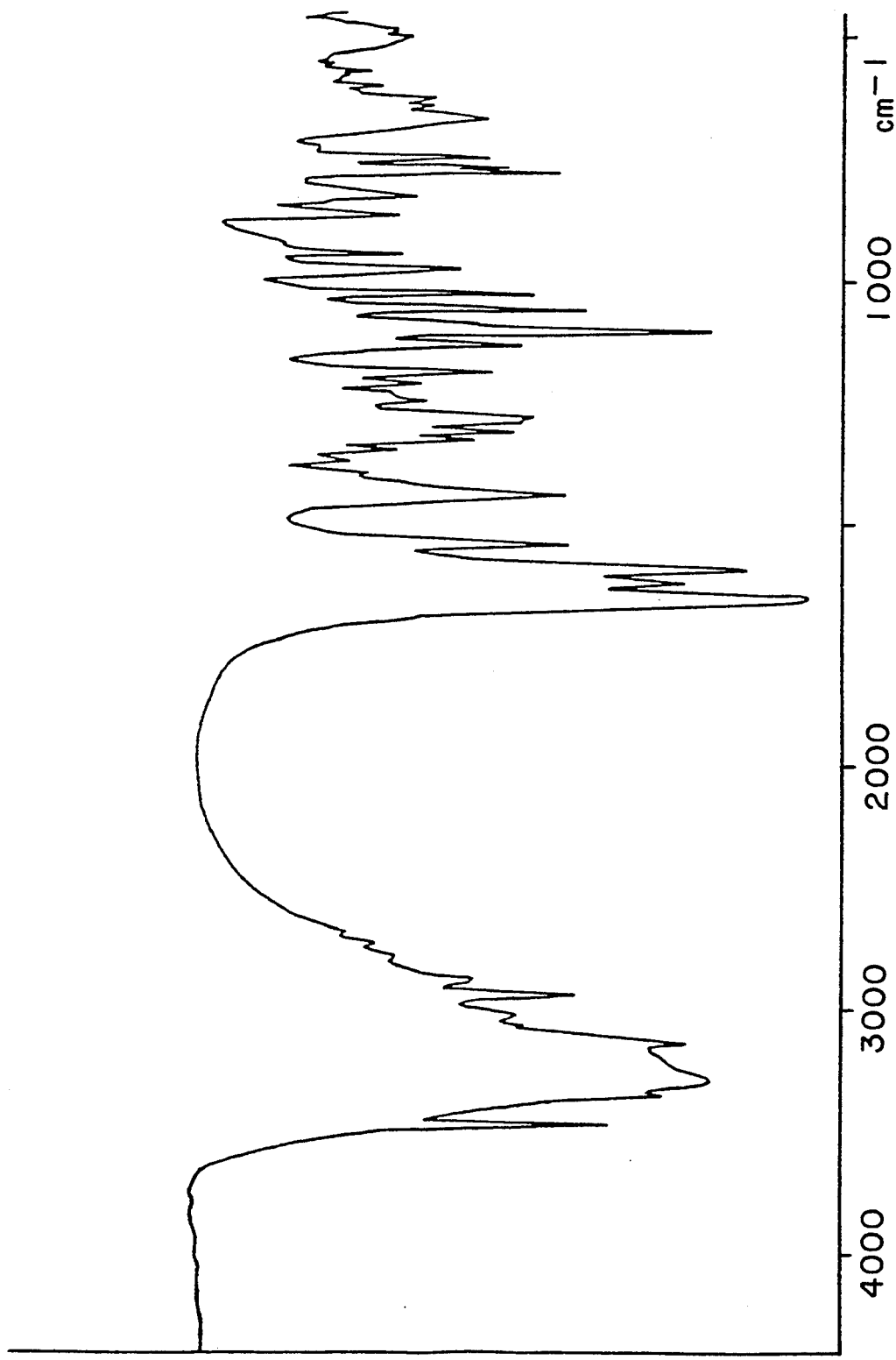
FIG. 2 is an IR absorption spectrum of Anhydrous Crystals A measured by an interference-type IR spectrophotometer.

0.5. g of Anhydrous Crystals A, as seed crystals, and 1.5 g of mizolibine monohydrate prepared in the same manner as in Comparative Example 1 were suspended into 20 ml of methanol. The suspension was heated to 68° C. with stirring, at which temperature the stirring was continued for 3 hours. After stopping the stirring, the suspension was cooled to 5° C. with ice-cooled water to collect deposited crystals by filtration. The crystals were washed with cold methanol and dried by allowing them to stand overnight at room temperature, then for 24 hours at 40° C. in vacuo, to obtain 1.86 g of crystals. IR absorption spectrum of the crystals by an interference-type IR spectrophotometer is as shown in FIG. 2. The crystals were Anhydrous Crystals A having a water content (the Karl Fisher method) of 0.12%.

Example 1

Figure 5:
FIG. 5 is a photograph of anhydrous crystals of mizolibine showing the crystal structure taken by a refractory microscope at 200 magnification.

5.0 g of purified mizolibine monohydrate crystals obtained in Comparative Example 1 was suspended into 50 ml of anhydrous ethanol. The suspension was refluxed in a boiling water bath for 60 minutes while stirring, followed by cooling in ice-cold water for 60 minutes. Deposited crystals were dried overnight at 40° C. in vacuo to obtain 4.61 g of anhydrous mizolibine crystals (water content: 0.11%). IR absorption spectrum of the crystals measured by an interference-type IR spectrophotometer (the KBr method) is as shown in FIG. 1. The crystal structure of the crystals are as shown in a photograph taken by a refractory microscope at 200 magnification given in FIG. 5, wherein 1 cm correspond to 10 μm.

Examples 2-11

Anhydrous mizolibine crystals of the present invention were prepared in the same manner as in Example 1, except that the conditions as to (1) the amount of mizolibine monohydrate (raw material), (2) the solvent, and (3) stirring conditions shown in Table 1 were employed. The yields and the water contents of the products which are the invention crystals were also given in Table 1.

All crystals of the present invention prepared in Examples 2-11 had the same IR absorption spectrum as that shown in FIG. 1.

Test Example 2 (Stability under high humidity conditions)

Monohydrate crystals of mizolibine (dried to a water content of 2.4% in vacuum at 40° C. for 48 hours in the presence of phosphorous pentoxide) and invention crystals, each 0.3 g, were placed in 3 ml open vials and left at 20° C. at 95% RH to investigate their weight increase by moisture absorption and the changes in water contents by the Karl Fisher method.

As a result, monohydrate crystals were found to have increased their weight by about 5% and contained water in an amount of about 6.5% in 24 hours, whereas the invention crystals exhibited almost no change in their weight and water content after 2 weeks.

Test Example 3 (Washing test)

5.0 g of purified mizolibine monohydrate crystals obtained in Comparative Example 1 was suspended into 50 ml of anhydrous ethanol ( ethanol purity: 99.5% ) and heated at 70° C. in a water bath with stirring, followed by cooling in ice-cold water to obtain 4.63 g of the invention crystals (water content: 0.12%).

As a control, a mixture of 4.0 g of purified mizolibine monohydrate crystals and 1.0 g of Anhydrous Crystals A as seed crystals was suspended into 50 ml of anhydrous methanol (methanol purity: 99.6%) and heated at 65° C. in a water bath with stirring, followed by cooling in ice-cold water to obtain 4.58 g of Anhydrous Crystals A (water content: 0.21%).

Teflon stirrer blades used in the above production were dismantled and set in 20 ml beakers to observe removability of attached crystals by washing with water. The blades were washed twice with 5 ml of water injected from a 10 ml dispenser (PIPETMAN P-5000: trade mark, product of Gilson Co.). This operation was repeated to collect each washing and to measure its absorbance at 279 nm. The washing operation was repeated until the absorbance became 0.28–0.29 or smaller, i.e. the 0.25–0.29 of absorbance which is a

TABLE 1

| Example No. | Raw material (g) | Solvent (ml) | Stirring conditions | Yield (g) | Water content (%) |
|---|---|---|---|---|---|
| 2 | 5.0 | Anhydrous ethanol (50) | 65° C., 2 hours | 4.6 | 0.12 |
| 3 | 5.0 | Anhydrous ethanol (100) | 50° C., 1 hour | 4.6 | 0.21 |
| 4 | 5.0 | Anhydrous ethanol (100) | Room temp., 30 min. | 4.5 | 0.18 |
| 5 | 5.0 | 90% ethanol (50) | In boiling water bath, 1 hour | 4.4 | 0.15 |
| 6 | 5.0 | 85% ethanol (50) | In boiling water bath, 1 hour | 4.3 | 0.21 |
| 7 | 5.0 | 80% ethanol (50) | In boiling water bath, 1 hour | 4.1 | 0.22 |
| 8 | 5.0 | 80% ethanol (50) | 50° C., 1 hour | 4.1 | 0.13 |
| 9 | 5.0 | 75% ethanol (25) | In boiling water bath, 1 hour | 4.2 | 0.21 |
| 10 | 5.0 | 75% ethanol (25) | 50° C., 1 hour | 4.1 | 0.20 |
| 11 | 5.0 | 50% ethanol (25) | In boiling water bath, 1 hour | 0.63 | 0.30 |

Test Example 1 (Heat stability)

Monohydrate crystals of mizolibine and invention crystals, each 0.5 g, in in 3 ml sealed vials were left at 65° C. to observe the change in their outward appearance. As a result, monohydrate crystals turned into dark green color and solidified in 24 hours, whereas the invention crystals exhibited no change in their outward appearance.

mizolibine solution of 5 μg/ml concentration at 279 nm. As a result, in the case of the invention crystals of mizolibine the absorbances was found to be 0.512 at the 8th washing, 0.107 at the 9th washing, 0.140 at 10th washing, and 0.083 at the 11th washing, demonstrating that almost all the compound attached to the blades was washed out at the 11th washing. In contrast, in the case of Anhydrous Crystals A, the absorbances was 0.494 at the 8th washing, 0.622 at the 9th washing, 0.552 at 10th washing, 0.975 at the 11th washing, 0.895 at 12th washing, 0.443 at 13th washing, 0.128 at 14th washing, and 0.150 at 15th washing. It is apparent that washing of 15 or more times are needed for the compound. It is therefore concluded that the invention crystals of mizolibine can more easily be washed out from the manufacturing apparatus and equipment in a shorter period of time discharging a less amount of washing wastes, thus ensuring a remarkable advantage over conventional products in an industrial scale manufacturing process.

The mizolibine anhydrous crystals of the present invention are very stable against heat and high humidity conditions and can easily be manufactured by using ethanol, which is a safer material than methanol used in conventional processes. The component attached to the manufacturing apparatus and equipment can very easily and efficiently be washed out. The preparations of the compound for oral administration possesses a good stability.

Obviously, numerous modifications and variations of the present invention are possible in light of the above teachings. It is therefore to be understood that within the scope of the appended claims, the invention may be practiced otherwise than as specifically described herein.

What is claimed is:

1. Anhydrous crystals of 4-carbamoyl-1-$\beta$-D-ribofuranosyl imidazolium-5-olate possessing the following characteristics:
   (1) water content determined by the Karl Fisher method:
       0.5% by weight or less, and
   (2) specific IR spectrum absorption peaks (measured by an interference-type IR spectrophotometer):
       3580, 1852, 1630, 1575, 1554 cm$^{-1}$ (standard deviation $\pm 2$ cm$^{-1}$).

* * * * *